US010800720B2

(12) United States Patent
Sharratt

(10) Patent No.: US 10,800,720 B2
(45) Date of Patent: Oct. 13, 2020

(54) PROCESS FOR THE REMOVAL OF HALOALKYNE IMPURITIES FROM (HYDRO)HALOCARBON COMPOSITIONS

(71) Applicant: MEXICHEM FLUOR S.A. DE C.V., San Luis Potosi (MX)

(72) Inventor: Andrew Paul Sharratt, Cheshire (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 0 days.

(21) Appl. No.: 16/480,045

(22) PCT Filed: Jan. 19, 2018

(86) PCT No.: PCT/GB2018/050156
§ 371 (c)(1),
(2) Date: Jul. 23, 2019

(87) PCT Pub. No.: WO2018/134607
PCT Pub. Date: Jul. 26, 2018

(65) Prior Publication Data
US 2019/0367434 A1 Dec. 5, 2019

(30) Foreign Application Priority Data
Jan. 23, 2017 (GB) .................. 1701099.2

(51) Int. Cl.
*C07C 17/395* (2006.01)
*C07C 17/38* (2006.01)
*C07C 21/18* (2006.01)
*C07C 17/20* (2006.01)
*C07C 17/25* (2006.01)

(52) U.S. Cl.
CPC .......... *C07C 17/395* (2013.01); *C07C 17/206* (2013.01); *C07C 17/25* (2013.01); *C07C 17/38* (2013.01)

(58) Field of Classification Search
CPC .................................................. C07C 17/395
See application file for complete search history.

(56) References Cited

U.S. PATENT DOCUMENTS

| | | | |
|---|---|---|---|
| 8,766,020 B2 | 7/2014 | Wang et al. | |
| 2005/0020862 A1 | 1/2005 | Tung et al. | |
| 2007/0112230 A1 | 5/2007 | Mukhopadhyay et al. | |
| 2009/0099396 A1 | 4/2009 | Mukhopadhyay et al. | |
| 2011/0190554 A1 | 8/2011 | Pigamo et al. | |
| 2011/0201852 A1 | 8/2011 | Pigamo et al. | |
| 2011/0251442 A1 | 10/2011 | Okamoto et al. | |
| 2011/0270000 A1 | 11/2011 | Bektesevic et al. | |
| 2011/0319677 A1 | 12/2011 | Kawaguchi et al. | |
| 2012/0022301 A1 | 1/2012 | Sedat et al. | |
| 2012/0065437 A1 | 3/2012 | Merkel et al. | |
| 2012/0083632 A1 | 4/2012 | Guillet et al. | |
| 2012/0116133 A1 | 5/2012 | Bossoutrot et al. | |
| 2012/0184785 A1 * | 7/2012 | Cottrell ............... C07C 17/087 570/153 |
| 2013/0092869 A1 | 4/2013 | Boussand | |
| 2013/0105724 A1 | 5/2013 | Boussand | |
| 2013/0274528 A1 | 10/2013 | Sharratt et al. | |
| 2014/0018582 A1 | 1/2014 | Sun et al. | |
| 2015/0259267 A1 | 9/2015 | Sun et al. | |
| 2015/0322317 A1 | 11/2015 | Collier et al. | |
| 2016/0230060 A1 | 8/2016 | Takahashi et al. | |

FOREIGN PATENT DOCUMENTS

| | | |
|---|---|---|
| CN | 104176747 | 12/2014 |
| CN | 105061136 | 11/2015 |
| EP | 2143702 | 1/2010 |
| FR | 2935702 | 3/2010 |
| WO | WO2008/030439 | 3/2008 |
| WO | WO2008/075017 | 6/2008 |
| WO | WO2009/003157 | 12/2008 |
| WO | WO2009/125199 | 10/2009 |
| WO | WO2009/125201 | 10/2009 |
| WO | WO2009/138764 | 11/2009 |
| WO | WO2010/129844 | 11/2010 |
| WO | WO2011/045559 | 4/2011 |
| WO | WO2011/139591 | 11/2011 |
| WO | WO2012/011609 | 1/2012 |
| WO | WO2012/051057 | 4/2012 |
| WO | WO2013/011291 | 1/2013 |
| WO | WO2013/184865 | 12/2013 |
| WO | WO2014/152325 | 9/2014 |
| WO | WO2014/159009 | 10/2014 |
| WO | WO2016/132111 | 8/2016 |
| WO | WO2017/079612 | 5/2017 |
| WO | WO-2018085512 A2 * | 5/2018 ........... C07C 17/395 |

OTHER PUBLICATIONS

International Search Report dated Apr. 16, 2018 from International Application Serial No. PCT/GB2018/050156 filed Jan. 19, 2018.
Written Opinion dated Apr. 16, 2018 from International Application Serial No. PCT/GB2018/050156 filed Jan. 19, 2018.

* cited by examiner

*Primary Examiner* — Medhanit W Bahta
(74) *Attorney, Agent, or Firm* — Ryan Kromholz & Manion, S.C.

(57) ABSTRACT

The invention relates to a process comprising contacting a composition comprising a (hydro)halocarbon and a compound of formula $R_f$—C=CX with a basic solution comprising an hydroxide, an alkoxide and/or an amide to reduce the concentration of $R_f$—C=CX, wherein $R_f$ is a perfluorinated alkyl group and X is H, F, Cl, Br, or I. The invention further relates to process for preparing a (hydro)halocarbon comprising (i) converting a starting material, optionally in the presence of HF and/or a catalyst, to a composition comprising the (hydro)halocarbon and a compound of formula $R_f$—C≡CX, wherein $R_f$ is a perfluorinated alkyl group and X is H, F, Cl, Br, or I; (ii) contacting the composition with a basic solution comprising an hydroxide, an alkoxide and/or an amide to reduce the concentration of the compound of formula $R_f$—C≡CX; and (iii) recovering the (hydro)halocarbon.

41 Claims, No Drawings

PROCESS FOR THE REMOVAL OF HALOALKYNE IMPURITIES FROM (HYDRO)HALOCARBON COMPOSITIONS

The present invention relates to processes for reducing the concentration of compounds of formula $R_f$—C≡CX in a composition comprising at least one (hydro)halocarbon.

The listing or discussion of a prior-published document in this specification should not necessarily be taken as an acknowledgement that the document is part of the state of the art or is common general knowledge.

(Hydro)halocarbons are typically used as refrigerant or propellant materials and as blowing agents. Over the last 20 years the variety of (hydro)halocarbons used in these applications has changed as it has been discovered that some such materials (e.g. difluorodichloromethane, CFC-12) deplete the earth's ozone layer, while others (e.g. 1,1,1,2-tetrafluoroethane, HFC-134a) have an unacceptably high action as a greenhouse gas.

Hydro(chloro)fluoroolefins have emerged as a class of compounds which may address these problems by providing good performance as refrigerants, propellant materials and/or as blowing agents, while also having a low ozone depletion potential and a low global warming potential.

For example, (hydro)fluoroalkenes, such as 2,3,3,3-tetrafluoropropene (HFO-1234yf), are increasingly being considered as working fluids in applications such as refrigeration, heat pumping, foam blowing, fire extinguishers/retardants, propellants and solvency (e.g. plasma cleaning and etching). However, the processes used to make (hydro) fluoroalkenes can lead to the generation of toxic and/or otherwise undesirable by-products.

At the elevated temperatures (e.g. in excess of 300° C.) typically considered to be necessary to achieve commercially desirable rates of reaction in the preparation of hydro (chloro)fluoroolefins, many side reactions become possible, including dehydrohalogenations, hydrohalogenations and rearrangements. Thus, the crude product mixture exiting the reaction train can contain many species other than the feeds and desired product.

For example, HFO-1234yf can be dehydrofluorinated under the reactions conditions in which it is prepared to yield 3,3,3-trifluoropropyne (trifluoromethylacetylene, TFMA). Although by-products such as TFMA may only be formed in small quantities relative to the desired product (e.g. HFO-1234yf), the presence of such by-products in HFO-1234yf compositions can impair its toxicity, stability (chemical/oxidative) and/or compatibility with refrigeration system components such as hoses or lubricants. Some applications therefore require very low levels of impurities. Unfortunately, some of the species formed have very similar physical properties to the desired (hydro)halocarbon compounds or associate with them, making normal separation methods, such as distillation or phase separation, ineffective.

Thus, there is a need for new methods for removing reaction by-products from (hydro)halocarbon compounds.

In a first aspect of the invention, there is provided a process comprising contacting a composition comprising a (hydro)halocarbon and a compound of formula $R_f$—C≡CX with a basic solution comprising an hydroxide, an alkoxide and/or an amide to reduce the concentration of $R_f$—C≡CX, wherein $R_f$ is a perfluorinated alkyl group and X is H, F, Cl, Br, or I.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will be taken. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. All percentage values are by weight unless otherwise specified.

The term '(hydro)halocarbon' refers to any saturated or unsaturated hydrocarbon where at least one hydrogen atom (and optionally all hydrogen atoms) are replaced by a fluorine, chlorine, bromine and/or iodine atom. In a preferred embodiment, the (hydro)halocarbon is unsaturated. For the avoidance of doubt, the composition comprising a (hydro)halocarbon (and a compound of formula $R_f$—C≡CX) can contain a single (hydro)halocarbon compound or a plurality of such compounds.

In a preferred embodiment, the (hydro)halocarbon is an hydrofluoroolefin (HFO). Preferably, the (hydro)halocarbon is a $C_{3-7}$ (hydro)haloalkene, such as a $C_{3-4}$ hydrohaloalkene. Examples of $C_{3-4}$ hydrohaloalkenes include hydrofluoropropenes, hydrochlorofluoropropenes, hydrofluorobutenes, hydrochlorofluorobutenes and (hydro)fluoropropenes. Advantageously, the (hydro)halocarbon is a hydrohalopropene.

In one embodiment, the hydrohalopropene is tetrafluoropropene and/or a chlorotrifluoropropene. Preferred tetrafluoropropenes are 2,3,3,3-tetrafluoropropene ($CF_3CF$=$CH_2$, HFO-1234yf) and/or E, Z or E/Z-1,3,3,3-tetrafluoropropene ($CF_3CH$=CHF, HFO-1234ze). Preferred chlorotrifluoropropenes are E, Z or E/Z-1-chloro-3,3,3-trifluoropropene ($CF_3CH$=CHCl, HCFO-1233zd) and/or 2-chloro-3,3,3-trifluoropropene ($CF_3CCl$=$CH_2$, HCFO-1233xf).

HFO-1234ze may exist as one of two configurational isomers, E or Z. HFO-1234ze as used herein refers to the isomers, E-HFO-1234ze or Z-HFO-1234ze, as well as any combinations or mixtures of such isomers.

HCFO-1233zd also may exist as one of two configurational isomers, E or Z. HCFO-1233zd as used herein refers to the isomers, E-HCFO-1233zd or Z-HCFO-1233zd, as well as any combinations or mixtures of such isomers.

$R_f$ in the compound of formula $R_f$—C≡CX typically is $C_{1-5}$ perfluorinated alkyl group, preferably a $C_1$-2 perfluorinated alkyl group such as a perfluorinated methyl group. In one embodiment, X=H, F or Cl, preferably H and Cl. Preferred compounds of formula $R_f$—C≡CX are 1-chloro-3,3,3-trifluoropropyne ($CF_3$C≡CCl) and 3,3,3-trifluoropropyne ($CF_3$C≡CCl, trifluoromethylacetylene, TFMA).

It is known that alkynes such as TFMA can be produced by the dehydrohalogenation of hydrohaloalkenes by bases. See, for example, pages 1530 to 1532 of 'March's Advanced Organic Chemistry' 6$^{th}$ Edition and EP-A-2143702. On the basis of such teaching, one might expect that contacting a composition comprising a (hydro)halocarbon and a compound of formula $R_f$—C≡CX with a basic solution comprising an hydroxide, alkoxide and/or amide would, if anything, increase the concentration of $R_f$—C≡CX. However, it has surprisingly been found that the use of a basic solution comprising an hydroxide, alkoxide and/or amide can effectively remove at least a portion of compounds of formula $R_f$—C≡CX from compositions as described above.

For the avoidance of doubt, it should be understood that the contacting step of the present invention is distinct from any earlier steps that may have been taken to prepare the (hydro)halocarbon. For example, the preparation of a $C_{3-7}$ (hydro)fluoroalkene by dehydrohalogenation of a corresponding $C_{3-7}$ hydro(halo)fluoroalkene using a basic solution comprising an hydroxide is known. See, for instance, WO 2008/075017. The contacting step of the process of the present invention is separate from any reaction step in which the $C_{3-7}$ (hydro)fluoroalkene (or other (hydro)halocarbon) is formed (such as described in WO 2008/075017), irrespective of whether any compound of formula $R_f$—C≡CX is also formed in such a reaction step.

A basic solution comprising an hydroxide, alkoxide and/or amide is used to reduce the concentration of $R_f$—C≡CX in the process of the invention. Preferably, the base is one or more of an alkali metal hydroxide, alkoxide or amide, an alkaline earth metal hydroxide, alkoxide or amide, $NR_4OH$, wherein R is, independently, H, $C_{1-10}$ alkyl, aryl (e.g. phenyl, naphthyl or pyridinyl) or arylalkyl group (e.g. benzyl or $C_{1-10}$ alkyl-substituted phenyl).

Advantageously, the base is selected from potassium hydroxide (KOH), sodium hydroxide (NaOH), calcium hydroxide (Ca(OH)$_2$), ammonium hydroxide (NH$_4$OH), potassium methoxide, sodium methoxide, potassium ethoxide, sodium ethoxide and sodium amide (NaNH$_2$). In a preferred embodiment, the base is sodium ethoxide, KOH, NaOH or Ca(OH)$_2$. Preferably, the base is KOH, NaOH or Ca(OH)$_2$. KOH and NaOH currently are most preferred.

The basic solution comprising an hydroxide, alkoxide and/or amide used in the contacting step of the invention typically has a concentration of from about 0.1 to about 10 M, preferably from about 0.2 to about 5 M, such as from about 0.5 to about 3 M, from about 0.5 to about 2 M, or from about 0.6 to about 2 M. Without being bound by theory, it is believed that the identified concentrations of are high enough for reaction with/removal of the compound of formula $R_f$—C≡CX and low enough so as not to react with the (hydro)halocarbon (e.g. to produce further $R_f$—C≡CX).

Further to this, a lower concentration of the basic solution is believed to have the advantage of reducing the likelihood of precipitation of any corresponding fluoride salts (e.g. NaF, KF, etc.).

Typically, the solvent for the basic solution comprising an hydroxide, alkoxide and/or an amide used in the contacting step is selected from water (i.e. an aqueous solution), alcohols (e.g. methanol, ethanol and n-propanol and i-propanol), diols, polyols (e.g. polyalkylene glycols such as PEG300), polar aprotic solvents (e.g. diglyme and N-methyl pyrrolidone), ethers and cyclic ethers (e.g. diethyl ether, dibutyl ether, tetrahydrofuran), esters (e.g. methyl acetate, ethyl acetate, etc.), linear, branched and cyclic alkanes (e.g. cyclohexane, methylcyclohexane), fluorinated derivatives thereof (e.g. hexafluoroisopropanol, perfluorotetrahydrofuran) and mixtures of the foregoing. In a preferred embodiment, the solvent is selected from water, alcohols and mixtures thereof. The currently preferred solvent is water, alone or in combination with any of the foregoing as a co-solvent.

The contacting step of the invention typically is carried out at a temperature of from about 0 to about 100° C., such as from about 10 to about 80° C., preferably from about 20 to about 60° C. The process may be carried out at subatmospheric, atmospheric or superatmospheric pressure, preferably atmospheric or superatmospheric pressure. Suitable pressures include from 0 bar to about 30 bar, such as from about 0.5 bar to about 20 bar, preferably from about 1 to about 5 or about 10 bar.

The composition typically is contacted with the basic solution comprising an hydroxide, alkoxide and/or amide for from about 1 second to about 4 hours, preferably from about 10 seconds to about 3 hours, such as from about 1 minute to about 180 minutes, preferably from about 2 to about 100 minutes, from about 5 to about 80 or from about 10 to about 60 minutes (e.g. from about 15 to about 45 minutes). This so-called residence time, together with other variables such as temperature of the contacting step and concentration of the basic solution comprising an hydroxide, alkoxide and/or amide, have been demonstrated (see later in the specification) to be important parameters in the process of the invention.

The composition comprising the (hydro)halocarbon and a compound of formula $R_f$—C≡CX can be in the liquid phase or in the gas phase (preferably the gas phase) when contacted with the basic solution comprising an hydroxide, alkoxide and/or amide.

Prior to contacting the basic solution comprising an hydroxide, alkoxide and/or amide, the composition preferably comprises at least about 90% by weight of the (hydro)halocarbon, such as at least about 95%, 98%, 99% or 99.5% by weight of the (hydro)halocarbon.

Prior to contacting the basic solution comprising an hydroxide and/or amide, the composition typically comprises about 10000 ppm or less of the compound of formula $R_f$—C≡CX, such as 5000 ppm or less. Preferably, the composition comprises less than about 4000 ppm, 3000 ppm, 2000 ppm, 1000 ppm, 800 ppm, 700 ppm, 600 ppm or 500 ppm or less of the compound of formula $R_f$—C≡CX prior to contacting the basic solution comprising an hydroxide, alkoxide and/or an amide.

The amount of the compound of formula $R_f$—C≡CX in the (hydro)halocarbon-containing composition is reduced in the process of the invention, typically by at least about 20% by weight of the composition, preferably by at least about 50%, 60%, 70%, 80%, 90% or 95% or more by weight of the composition.

Following contacting the basic solution comprising an hydroxide, alkoxide and/or amide, the composition typically comprises from 0 to about 1000 ppm of the compound of formula $R_f$—C≡CX, such as from 0 to about 500 ppm.

Preferably, the composition comprises less than about 400 ppm, 300 ppm, 200 ppm, 100 ppm, 50 ppm, 40 ppm, 30 ppm, 20 ppm, 10 ppm or 5 ppm or less of the compound of formula $R_f$—C≡CX following contacting the basic solution comprising an hydroxide, alkoxide and/or an amide.

In one embodiment, the contacting step is carried out in the presence of a phase transfer catalyst. The term "phase transfer catalyst", as used herein, means a substance that facilitates the migration of a chemical compound from one phase into another phase. The phase transfer catalyst can be ionic or neutral and is typically selected from the group consisting of crown ethers, onium salts, cryptands and polyalkylene glycols and derivatives thereof (e.g. fluorinated derivatives thereof).

Typically, the amount of catalyst used is from about 0.001 to about 20 wt % by weight of the composition, such as from about 0.01 to about 10 wt %, for example from about 0.5 to about 5 wt %.

Crown ethers are cyclic molecules in which ether groups are connected by dimethylene linkages. Useful crown ethers include 18-crown-6, 15-crown-5 and 12-crown-4. Derivatives of the above crown ethers are also useful, such as dibenzyl-18-crown-6, dicyclohexanyl-18-crown-6, dibenzyl-24-crown-8 and dibenzyl-12-crown-4. Other compounds analogous to the crown ethers and useful for the same purpose are compounds which differ by the replacement of one or more of the oxygen atoms by other kinds of donor atoms, particularly N or S. Fluorinated derivatives of all the above may also be used.

Cryptands are another class of compounds useful in the base-mediated dehydrohalogenation as phase transfer catalysts. These are three dimensional polymacrocyclic chelating agents that are formed by joining bridgehead structures with chains that contain properly spaced donor atoms. The donor atoms of the bridges may all be O, N, or S, or the compounds may be mixed donor macrocycles in which the bridge strands contain combinations of such donor atoms. Suitable cryptands include bicyclic molecules that result from joining nitrogen bridgeheads with chains of (—OCH$_2$CH$_2$—) groups, for example as in [2.2.2]cryptand (4,7,13,16,21,24-hexaoxa-1,10-diazabicyclo[8.8.8]hexacosane, available under the brand names Kryptand 222 and Kryptofix 222).

Onium salts that may be used as catalysts in the base-mediated dehydrohalogenation process include quaternary phosphonium salts and quaternary ammonium salts, which may be represented by the formulae $R^1R^2R^3R^4P^+Z^-$ and $R^1R^2R^3R^4N^+Z^-$, respectively. In these formulae, each of $R^1$, $R^2$, $R^3$ and $R^4$ typically represent, independently, a $C_{1-10}$ alkyl group, an aryl group (e.g. phenyl, naphthyl or pyridinyl) or an arylalkyl group (e.g. benzyl or $C_{1-10}$ alkyl-substituted phenyl), and $Z^-$ is a halide or other suitable counterion (e.g. hydrogen sulphate).

Specific examples of such phosphonium salts and quaternary ammonium salts include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulphate, tetra-n-butylphosphonium chloride, tetraphenylphosphonium bromide, tetraphenylphosphonium chloride, triphenylmethylphosphonium bromide and triphenylmethylphosphonium chloride. Benzyltriethylammonium chloride is preferred for use under strongly basic conditions. Quaternary ammonium chloride salts are a preferred class of onium salts for use as phase transfer catalysts, for example Aliquat 336.

Other useful onium salts include those exhibiting high temperature stabilities (e.g. up to about 200° C.), for example 4-dialkylaminopyridinium salts, tetraphenylarsonium chloride, bis[tris(dimethylamino)phosphine]iminium chloride and tetrakis[tris(dimethylamino)phosphinimino] phosphonium chloride.

Polyalkylene glycol compounds useful as phase transfer catalysts may be represented by the formula $R^6O(R^5O)_mR^7$ wherein $R^5$ is a $C_{1-10}$ alkylene group, each of $R^6$ and $R^7$ are, independently, H, a $C_{1-10}$ alkyl group, an aryl group (e.g. phenyl, naphthyl or pyridinyl) or an arylalkyl group (e.g. benzyl or $C_{1-10}$ alkyl-substituted phenyl), and m is an integer of at least 2. Preferably, both $R^6$ and $R^7$ are the same, for example they may both be H.

Such polyalkylene glycols include diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, monoalkyl glycol ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers of such glycols, and polyalkylene glycols such as polyethylene glycol (average molecular weight about 300) and polyethylene glycol (average molecular weight about 400) and the dialkyl (e.g. dimethyl, dipropyl, dibutyl) ethers of such polyalkylene glycols.

Combinations of phase transfer catalysts from within one of the groups described above may also be useful as well as combinations or mixtures from more than one group.

In one embodiment, the composition comprising a (hydro)halocarbon and a compound of formula $R_f$—C≡CX may be a product stream from a process for producing the (hydro)halocarbon. Accordingly, the composition typically contains a target or desired (hydro)halocarbon, such as a hydrohalopropene (for instance a tetrafluoropropene, e.g. HFO-1234yf or HFO-1234ze, and/or a chlorotrifluoropropene, e.g. HCFO-1233zd or HCFO-1233xf) and one or more (undesired) (hydro)halocarbon by-products. The process can be conducted as a batch reaction, a continuous reaction or as a semi-continuous reaction.

Examples of such (hydro)halocarbon by-products, for instance in processes for producing tetrafluoropropenes (e.g. HFO-1234yf) and/or chlorotrifluoropropene (e.g. HCFO-1233xf), include pentafluoropropenes (e.g. $CF_3CFH$=CFH, HFO-1225ye), pentafluoropropanes (e.g. HFC-245eb and/or HFC-245fa and/or HFC-245cb), chlorotetrafluoropropanes (e.g. HCFC-244bb) and hexafluoropropanes (e.g. $CF_3CFHCF_2H$, HFC-236ea).

Unexpectedly, it has been found that the contacting step of the invention is effective at reducing the concentration of not only the compound of formula $R_f$—C≡CX, but it can also be effective at reducing the concentration of one or more by-products present in a composition containing the target (hydro)halocarbon, compound of formula $R_f$—C≡CX and (hydro)halocarbon by-product. This results in an increase in selectivity and/or yield for the desired (hydro) halocarbon. Preferably, the concentration of any saturated (hydro)halocarbon by-products is reduced relative to the desired (hydro)halocarbon.

The amount of (hydro)halocarbon by-product in the desired (hydro)halocarbon-containing composition typically is reduced in the process of the invention by at least about 20% by weight of the composition, preferably by at least about 50%, 60%, 70%, 80%, 90% or 95% or more by weight of the composition.

Following contacting the basic solution comprising an hydroxide, alkoxide and/or amide, the composition typically comprises from 0 to about 1000 ppm of the compound of the (hydro)halocarbon by-product, such as from 0 to about 500 ppm. Preferably, the composition comprises less than about 400 ppm, 300 ppm, 200 ppm, 100 ppm, 50 ppm, 40 ppm, 30 ppm, 20 ppm, 10 ppm or 5 ppm or less of the (hydro) halocarbon by-product following contacting the basic solution comprising an hydroxide, alkoxide and/or amide.

In a second aspect of the invention, there is provided a process for preparing a (hydro)halocarbon comprising:
(i) converting a starting material, optionally in the presence of HF and/or a catalyst, to a composition comprising the (hydro)halocarbon and a compound of formula $R_f$—C≡CX, wherein $R_f$ is a perfluorinated alkyl group and X is H, F, Cl, Br, or I;
(ii) contacting the composition with a basic solution comprising an hydroxide, an alkoxide and/or an amide to reduce the concentration of the compound of formula $R_f$—C≡CX; and
(iii) recovering the (hydro)halocarbon.

For the avoidance of doubt, the information described above in connection with the first aspect invention, for example regarding the composition comprising a (hydro) halocarbon and a compound of formula $R_f$—C≡CX and the contacting step, is also applicable to the second aspect of the invention. Further embodiments of the second aspect of the invention are described hereinafter.

The conversion of the starting material to the (hydro) halocarbon and $R_f$—C≡CX impurity in step (i) preferably comprises an hydrogenation reaction, a dehydrohalogenation reaction, an isomerisation reaction and/or a fluorination reaction.

In an embodiment, the composition comprising the (hydro)halocarbon and a compound of formula $R_f$—C≡CX is prepared by an hydrogenation reaction.

Such hydrogenation reaction(s) may be carried out in the liquid or vapour phase, preferably the vapour phase, typically at a temperature of from about −50 to about 275° C. Preferred temperatures for liquid phase hydrogenation are from about −50 to about 50° C., e.g. from about 15 to about 40° C. Preferred temperatures for vapour phase hydrogenation are from about 0 to about 250° C., such as from about 20 to about 200° C., e.g. from about 50 to about 150° C.

The hydrogenation reaction(s) may be carried out in the presence of a fluorinated polar aprotic solvent, particularly when carried out in the liquid phase. Suitable solvents include HFCs (e.g. 134a) and PFCs (e.g. perfluorodecalin).

The hydrogenation reaction(s) may be carried out at atmospheric, sub- or super-atmospheric pressure, preferably super-atmospheric pressure. For example, the hydrogenation may be carried out at a pressure of from about 0 to about 40 bara, such as from about 1 to about 30 bara, e.g. from about 5 to about 20 bara.

The ratio of hydrogen:reagents is suitably from about 0.1:1 to about 40:1, such as from about 1:1 to about 20:1, preferably, from about 1.1:1 to about 10:1, e.g. from 1.5:1 to about 5:1.

The hydrogenation reaction(s) typically are carried out in the presence of a catalyst. Suitable hydrogenation catalysts include those comprising the transition metals nickel (Ni), palladium (Pd), platinum (Pt), rhenium (Re), rhodium (Rh), ruthenium (Ru) and mixtures thereof. Such catalysts may be supported on, for example, alumina, titania, silica, zirconia, fluorides of the foregoing, calcium fluoride, carbon or barium sulphate, or they may be unsupported, for example Raney Ni or Pd metal produced by reduction of $PdO_2$. Examples of catalysts suitable for use in the present invention include Pd/alumina, Pd/barium sulphate, Pd/C and chlorotris(triphenylphosphine)rhodium(I). Preferably, the catalyst is palladium supported on carbon (Pd/C) or chlorotris(triphenylphosphine)rhodium(I) (Wilkinson's catalyst) or platinum supported on alumina ($Pt/Al_2O_3$) or Adams catalyst, $PtO_2$, reduced in situ to platinum metal. When Pd/C is used as the catalyst, the Pd is present in an amount of from about 0.01 to about 10% by weight of the catalyst, such as from about 0.1 to about 5%

The hydrogenation catalyst typically is used in an amount of from about 0.01 to about 30% by weight based on the total weight of the components which make up steps (a) and (c), such as from about 0.1 to about 10%. When Pd/C is used as the catalyst, the Pd is present in an amount of from about 0.01 to about 10% by weight of the catalyst, such as from about 0.1 to about 5%.

In the vapour phase the contact time for the catalyst may be from about 1 to about 200 seconds, such as from about 2 to about 150 seconds. In the liquid phase the contact time for the catalyst with suitably is from about 1 to about 180 minutes, such as from about 2 to about 60 minutes.

In an embodiment, the composition comprising the (hydro)halocarbon and a compound of formula $R_f$—C≡CX is prepared by a dehydrohalogenation reaction.

The dehydrohalogenation reaction may be carried out by pyrolysing the starting material to produce the composition comprising the (hydro)halocarbon and a compound of formula $R_f$—C≡CX. By the term "pyrolysing" or "pyrolysis", as used herein, we include the meaning of chemical change produced by heating in the absence of catalyst. By absence of catalyst, we include the meaning that no material or treatment is added to the pyrolysis reactor that increases the reaction rate by reducing the activation energy of the pyrolysis process.

Any suitable reactor can be used for the pyrolysis, for example a cylindrical tube, either straight or coiled. Preferred pyrolysis reactors include those in which the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, has an open structure like that of Raschig Rings or other packings with a high free volume to avoid the accumulation of coke and to minimize pressure drop, and permits a generally free flow of gas. In some embodiments of this invention, the reactor packing is in cartridge disposition for ease of insertion and removal. In some embodiments of this invention, the pyrolysis reactor is substantially empty which means that the free volume of the reaction zone (the volume of the reaction zone minus the volume of the material that makes up the reactor packing) is at least about 80%, preferably at least about 90% and more preferably at least about 95%. In some embodiments, the pyrolysis reactor is comprised of materials which are resistant to corrosion including stainless steel, Hastelloy®, Inconel®, Monel®, gold, or gold-lined or quartz.

The dehydrohalogenation reaction of step (i) preferably comprises dehydrofluorination process and/or dehydrochlorination depending on the starting material and the corresponding (hydro)halocarbon product. The pyrolysis temperature for dehydrofluorination typically is higher than for dehydrochlorination. For example, dehydrofluorinating pyrolysis may be conducted at a temperature of from about 600° C. to about 900° C. and dehydrochlorinating pyrolysis may be conducted at a temperature of from about 400° C. to about 700° C.

In an embodiment, the dehydrohalogenation reactions are catalysed. Such reactions may be carried out in the liquid or vapour phase, preferably the vapour phase. A temperature of from about −25 to about 700° C. may be used. Preferred temperatures for the liquid phase are from about 0 to about 180° C., e.g. from about 15 to about 120° C. Preferred temperatures for vapour phase dehydrohalogenation are from about 100 to about 650° C., such as from about 200 to about 600° C., e.g. from about 300 to about 500° C.

Catalysed dehydrohalogenation reactions may be carried out at atmospheric, sub- or super-atmospheric pressure, preferably atmospheric or super-atmospheric pressure. For example, the dehydrohalogenation may be carried out at a pressure of from about 0 to about 40 bara, such as from about 1 to about 30 bara, e.g. from about 1 or 5 to about 20 bara.

Preferably, the catalyst is stable in the presence of HF and/or HCl. Suitable catalysts include metal and carbon based catalysts such as those comprising activated carbon (including acid-washed carbon, activated carbon and three dimensional matrix carbonaceous materials), main group (e.g. alumina-based catalysts) and transition metals, such as chromia-based catalysts (e.g. zinc/chromia) or nickel-based catalysts (e.g. nickel mesh). Examples of such catalysts include alumina, fluorided alumina, aluminum fluoride, aluminum chlorofluoride; metal compounds supported on alumina, fluorided alumina, aluminum fluoride, or aluminum chlorofluoride; chromium oxide ($Cr_2O_3$), fluorided chromium oxide, and cubic chromium trifluoride; oxides, fluorides, and oxyfluorides of magnesium, zinc and mixtures of magnesium and zinc and/or aluminum; lanthanum oxide and fluorided lanthanum oxide; carbon, and metal compounds supported on carbon. The metal compounds can be oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. In some embodiments of this invention, the dehydrohalogenation catalyst comprises alkali metal salt supported on chromium oxide.

The catalyst used may be used in an amount of from about 0.01 to about 50% by weight, such as from about 0.1 to about 30%, for example from about 0.5 to about 20%, based on the weight of the reagents. The contact time with the catalyst in the catalysed reaction suitably is from about 1 to about 500 seconds, such as from about 5 to about 400 seconds.

The dehydrohalogenation can be carried out in any suitable apparatus, such as a static mixer, a stirred tank reactor or a stirred vapour-liquid disengagement vessel. Preferably, the apparatus is made from one or more materials that are resistant to corrosion, e.g. Hastelloy® or Inconel®. The process may be carried out batch-wise or (semi-) continuously, preferably (semi-) continuously.

In an embodiment, the composition comprising the (hydro)halocarbon and a compound of formula $R_f$—C≡CX is prepared by an isomerisation reaction. Suitable reaction conditions and catalysts include those as described above in relation to the dehydrohalogenation reactions, optionally at somewhat lower temperatures. Suitable conditions for isomerisation reactions are described in, for example, WO 2008/125825 and WO 2015/059500. By the term 'isomerisation reaction', we include structural and geometric isomerisation, such as structural isomerisation of $CF_2CH=CF_2$ (HFO-1234zc) to HFO-1234ze and geometric isomerisation of Z-HFO-1234ze to E-HFO-1234ze.

In an embodiment, the composition comprising the (hydro)halocarbon and a compound of formula $R_f$—C≡CX is prepared by a fluorination reaction. Suitable reaction conditions and catalysts include those as described above in relation to the dehydrohalogenation reactions, but in the presence of a fluorination agent such as HF. Typically, the HF is used in a molar excess compared to the starting material, such as from about 1:1 to about 70:1, preferably from about 2:1 to about 60:1, such as from about 3:1 to about 50:1, for example from about 5:1 to about 40:1. Suitable conditions for fluorination reactions are described in, for example, EP-A-2154122 and WO 2011/077394.

The (hydro)halocarbon produced in step (i) may be a $C_{3-7}$ (hydro)haloalkene, preferably a hydrohalopropene, such as a chlorotrifluoropropene and/or a tetrafluoropropene.

Preferably, the starting material comprises one or more of $CCl_3CH_2CCl_2H$ (HFC-240fa), $CF_3CH_2CFClH$ (HCFC-244fa), $CF_3CH_2CF_2H$ (HFC-245fa), $CF_3CF_2CH_3$ (HFC-245cb), $CF_3CFHCFH_2$ (HFC-245eb), $CF_3CFClCH_3$ (HCFC-244bb), HCFO-1233xf, a tetrachloropropene (HCO-1230), Z-HFO-1234ze, Z-HCFO-1233zd, HFO-1234zc and $CCl_3CClHCClH_2$ (HFC-240db). The starting material may also be $CF_3CHClCH_2Cl$ (HCFC-243db).

Advantageously, the hydrohalopropene is HCFO-1233zd and/or HFO-1234ze, and wherein the starting material comprises one or more of $CCl_3CH_2CCO_2H$ (HFC-240fa), $CF_3CH_2CFClH$ (HCFC-244fa) and $CF_3CH_2CF_2H$ (HFC-245fa), such as described in, for example, US 2014/228600, which is hereby incorporated by reference. In a further embodiment, the hydrohalopropene can be E-HCFO-1233zd and wherein the starting material comprises E-HCFO-1233zd, or the the hydrohalopropene can be E-HFO-1234ze, and wherein the starting material comprises one or more of Z-HFO-1234ze or HFO-1234zc.

Preferably, the hydrohalopropene is HFO-1234yf and the starting material comprises one or more of $CF_3CF_2CH_3$ (HFC-245cb), $CF_3CFHCFH_2$ (HFC-245eb), $CF_3CFClCH_3$ (HCFC-244bb), HCFO-1233xf, a tetrachloropropene (HCO-1230) and $CCl_3CClHCClH_2$ (HFC-240db), such as described in WO 2008/04096 and WO 2010/123154, which are hereby incorporated by reference. The starting material for preparing HFP-1234yf may also be $CF_3CHClCH_2Cl$ (HCFC-243db).

Advantageously, the hydrohalopropene is HCFO-1233xf and the starting material comprises a tetrachloropropene (HCO-1230) and/or $CCl_3CClHCClH_2$ (HFC-240db), such as described in WO 2011/077394, which is hereby incorporated by reference.

Preferably, the (hydro)halocarbon is HCFC-244bb and the starting material comprises one or more of HCFO-1233xf, a tetrachloropropene (HCO-1230) and $CCl_3CClHCClH_2$ (HFC-240db), such as described in WO 2007/125199, which is incorporated herein by reference.

In some embodiments of this invention, the composition comprising a (hydro)halocarbon and a compound of $R_f$—C≡CX is mixed with basic solution comprising an hydroxide, alkoxide and/or amide, optionally in the presence of a suitable solvent, in a vessel equipped with an agitator. For example, (hydro)halocarbon containing $R_f$—C≡CX impurity may be contacted with basic solution comprising an hydroxide, alkoxide and/or amide under a suitable amount of pressure to maintain liquid phase of the (hydro)halocarbon and the basic solution comprising an hydroxide, alkoxide and/or amide in a vessel. The contents of the contacting vessel may be agitated to provide contact between the (hydro)halocarbon and the basic solution comprising an hydroxide, alkoxide and/or amide.

In some embodiments, the contacting step can be carried out by contacting a gaseous mixture of (hydro)halocarbon and $R_f$—C≡CX impurity with basic solution comprising an hydroxide, alkoxide and/or amide. For example, the mixture comprising (hydro)halocarbon and $R_fC$≡CX impurity may be bubbled into the basic solution comprising an hydroxide, alkoxide and/or amide as a gas in a stirred vessel. The (hydro)halocarbon is then allowed to leave the contacting vessel, optionally through a condenser, where it can be further purified or recovered.

In some embodiments, the contacting step is conducted in a column packed with materials such as helices, rings, saddles, spheres or other formed shapes fabricated from glass, plastic, or ceramics. The mixture comprising (hydro)halocarbon and $R_f$—C≡CX impurity enters the bottom of the column as a vapour. The basic solution comprising an hydroxide, alkoxide and/or amide enters the top of the column, for example, by means of a pump connected to a reservoir of said basic solution comprising an hydroxide, alkoxide and/or amide. The $R_f$—C≡CX impurity in the (hydro)halocarbon is then removed by contacting with basic solution comprising an hydroxide, alkoxide and/or amide in the column and the (hydro)halocarbon vapour, with reduced $R_f$—C≡CX impurity, passes out the top of the column and is then collected. The basic solution comprising an hydroxide, alkoxide and/or amide passes out the bottom of the column and returns to the reservoir.

The (hydro)halocarbon is recovered in step (iii) by any suitable means including, for example, distillation and/or phase separation.

The process of the invention may comprise one or more additional purification steps, such as distillation, condensation, scrubbing, phase separation, acid removal, polishing and/or drying.

HF and optionally HCl may be present in the composition resulting from the converting step. Preferably, at least some of the HF, and optionally HCl, in the composition is removed prior to the contacting step. The acid can be removed by, for example, flash separation, aqueous scrubbing and/or distillation. Where bulk removal of HF occurs prior to the contacting step (ii), residual HF (and optionally HCl) is advantageously removed by the contacting step.

If the basic solution comprising an hydroxide, alkoxide and/or an amide used in step (ii) is aqueous, it is preferable to have a drying step. Drying of the (hydro)halocarbon can be achieved by known methods, such as treatment with sulphuric acid and/or contact with a porous medium, such as silica, aluminium-containing adsorbents (e.g. zeolites) or activated carbon.

As will be understood by the skilled person, any of the preferred and alternative embodiments presented above may be applicable to any of the described aspects of the invention.

The invention is illustrated by the following non-limiting Examples.

EXAMPLES

Experimental

A feed mixture was prepared by adding TFMA (2.5 g) to HFO-1234yf (499.98 g). This mixture, containing 0.50% wt TFMA, was used for all experiments.

The solid base was accurately weighed into a 100 ml Hastelloy C22 autoclave and dissolved in a known weight of deionised water. If used, the phase transfer catalyst was also added at this point. The vessel was sealed, purged with nitrogen and evacuated. It was then pressurised (4-4.5 Barg) with the HFO-1234yf/TFMA feed mixture. The contents of the vessel were then stirred at 1000 rpm and heated to the desired temperature over a period of 4 to 5 minutes. Once at the desired temperature, samples of the gas in the headspace of the vessel were periodically withdrawn and analysed by gas chromatography.

Results

The experiments were performed using a variety of basic reagents at different concentrations, temperatures and both in the presence and absence of a phase transfer catalyst (Aliquat 336). The results are set out in Tables 1 to 8.

TABLE 1

(Example 1)

| Base | KOH (85 wt %) 2.1 g |  |
| --- | --- | --- |
| Concentration (mol/L) | 0.64 |  |
| Temperature (° C.) | 50 |  |

| Time (mins) | TFMA (wt %) | 1234yf (%) |
| --- | --- | --- |
| 0 | 0.50 | 99.46 |
| 33.66 | 0.37 | 99.60 |
| 71 | 0.27 | 99.71 |
| 129 | 0.19 | 99.81 |
| 177 | 0.13 | 99.87 |

TABLE 2

(Example 2)

| Base | KOH (85 wt %) 4.1 g |  |
| --- | --- | --- |
| Concentration (mol/L) | 1.24 |  |
| Temperature (° C.) | 50 |  |

| Time (mins) | TFMA (wt %) | 1234yf (%) |
| --- | --- | --- |
| 0 | 0.50 | 99.43 |
| 27.5 | 0.27 | 99.68 |
| 52 | 0.20 | 99.78 |
| 90 | 0.13 | 99.86 |
| 193 | 0.04 | 99.95 |

TABLE 3

(Example 3)

| Base | KOH (85 wt %) 2.1 g |  |
| --- | --- | --- |
| Concentration (mol/L) | 0.64 |  |
| Temperature (° C.) | 70 |  |

| Time (mins) | TFMA (wt %) | 1234yf (%) |
| --- | --- | --- |
| 0 | 0.50 | 99.48 |
| 25 | 0.20 | 99.80 |
| 63 | 0.05 | 99.95 |
| 104 | 0.02 | 99.98 |
| 130 | 0.01 | 99.99 |

TABLE 4

(Example 4)

| Base | KOH (85 wt %) 4.2 g |  |
| --- | --- | --- |
| Concentration (mol/L) | 1.27 |  |
| Temperature (° C.) | 70 |  |

TABLE 4-continued (Example 4)

| Time (mins) | TFMA (wt %) | 1234yf (%) |
|---|---|---|
| 0 | 0.50 | 99.49 |
| 16 | 0.19 | 99.81 |
| 50 | 0.05 | 99.95 |
| 83 | 0.02 | 99.98 |
| 118 | 0.01 | 99.99 |

TABLE 5

(Example 5)

| Base | KOH (85 wt %) 4.0 g |
|---|---|
| Concentration (mol/L) | 1.21 |
| Temperature (° C.) | 50 |
| Phase transfer catalyst | Aliquat 336 0.1 g |

| Time (mins) | TFMA (wt %) | 1234yf (%) |
|---|---|---|
| 0 | 0.50 | 99.48 |
| 25 | 0.17 | 99.83 |
| 62 | 0.05 | 99.95 |
| 88 | 0.02 | 99.98 |
| 124 | 0.01 | 99.99 |

TABLE 6

(Example 6)

| Base | NaOH (85 wt %) 2.1 g |
|---|---|
| Concentration (mol/L) | 1.03 |
| Temperature (° C.) | 50 |

| Time (mins) | TFMA (wt %) | 1234yf (%) |
|---|---|---|
| 0 | 0.50 | 99.46 |
| 22 | 0.43 | 99.54 |
| 74 | 0.27 | 99.71 |
| 103 | 0.19 | 99.80 |
| 178 | 0.10 | 99.89 |

TABLE 7

(Example 7)

| Base | NaOH (85 wt %) 4.0 g |
|---|---|
| Concentration (mol/L) | 1.97 |
| Temperature (° C.) | 70 |
| Phase transfer catalyst | Aliquat 336 0.1 g |

| Time (mins) | TFMA (wt %) | 1234yf (%) |
|---|---|---|
| 0 | 0.50 | 99.47 |
| 13 | 0.23 | 99.75 |
| 27 | 0.07 | 99.93 |
| 71 | 0.01 | 99.99 |
| 130 | 0.00 | 100.00 |

TABLE 8

(Example 8)

| Base | CaO 2.55 g |
|---|---|
| Concentration (mol/L) | 0.83 |
| Temperature (° C.) | 50 |

| Time (mins) | TFMA (wt %) | 1234yf (%) |
|---|---|---|
| 0 | 0.54 | 99.43 |
| 39 | 0.51 | 99.46 |
| 76 | 0.50 | 99.47 |
| 130 | 0.48 | 99.48 |
| 180 | 0.47 | 99.50 |

It can be seen that treatment with a base is very effective in reducing the absolute concentration of TFMA in the mixture and increasing the HFO-1234yf content of the mixture relative to TFMA overall.

A reduction in other trace impurities was also observed following treatment with a base. The results of reducing other impurities are summarised in Tables 9 and 10.

TABLE 9

(Example 9)

| Base | NaOH (85 wt %) 4.0 g |
|---|---|
| Concentration (mol/L) | 1.97 |
| Temperature (° C.) | 70 |
| Phase transfer catalyst | Aliquat 336 0.1 g |

| Species | Area Counts in 1234yf feed material | Area counts in 1234yf after treatment | Reduction (%) |
|---|---|---|---|
| Z-1225ye | 14.81 | 3.00 | 79.8 |
| 236ea | 2.02 | 0.00 | 100.0 |
| 245eb | 21.75 | 0.00 | 100.0 |

TABLE 10

(Example 10)

| Base | KOH (85 wt %) 4.1 g |
|---|---|
| Concentration (mol/L) | 1.24 |
| Temperature (° C.) | 50 |

| Species | Area Counts in 1234yf feed material | Area counts in 1234yf after treatment | Reduction (%) |
|---|---|---|---|
| 236ea | 2.55 | 0.27 | 89.4 |
| 245eb | 23.97 | 0.00 | 100.0 |

The process of the invention is therefore also effective in reducing the levels of R-1225ye(Z), R-236ea and R-245eb in a composition comprising HFO-1234yf.

Experimental

A feed mixture was prepared by adding TFMA (1.25 g) to an HFO (250 g). These mixtures, containing 0.50% wt TFMA, were used for all experiments.

In a typical scrubbing experiment the base was accurately weighed into a 100 ml Hastelloy C22 autoclave and dissolved in a known weight of deionised water or solvent. If used, any further additives e.g. KF or catalysts were also added at this point. The vessel was then sealed, purged with nitrogen, evacuated and heated to the desired temperature over 5 minutes. Once at temperature the vessel was then pressurised with the HFO/TFMA feed mixture. The contents of the vessel were then stirred at 1000 pm and samples of the gas in the headspace of the vessel were periodically withdrawn and analysed by gas chromatography.

Results

The experiments were performed using a variety of basic reagents and hydrofluoroolefins (HFOs). The results are set out in Tables 11 to 15.

TABLE 11

(Example 11 - TFMA removal from E-1234ze)

| Base | KOH (85 wt %) 4.1 g |
|---|---|
| Concentration (mol/l) | 1.24 |
| Temperature (° C.) | 50 |

| Time (mins) | TFMA (wt %) | E-1234ze (%) |
|---|---|---|
| 0 | 0.50 | 99.2 |
| 1 | 0.46 | 99.2 |
| 9.5 | 0.45 | 99.0 |
| 37 | 0.35 | 98.9 |
| 62 | 0.29 | 99.0 |
| 91 | 0.21 | 99.2 |

TABLE 12

(Example 12 - TFMA removal from 1233xf*)

| Base | KOH (85 wt %) 4.1 g |
|---|---|
| Concentration (mol/l) | 1.24 |
| Temperature (° C.) | 50 |

| Time (mins) | TFMA (wt %) | E-1233xf (%) |
|---|---|---|
| 0 | 0.50 | 98.79 |
| 60 | 0.16 | 99.29 |

TABLE 13

(Example 13 - TFMA removal from 1234yf with Sodium Ethoxide in Ethanol)

| Base solution | 20 g 21% NaOEt/Ethanol + 40 g Ethanol |
|---|---|
| Temperature (° C.) | 50 |

| Time (mins) | TFMA (%) | E-1234yf (%) |
|---|---|---|
| 0 | 0.50 | 98.96 |
| 10 | 0.10 | 99.73 |
| 30 | 0.03 | 99.89 |
| 56 | 0.01 | 99.95 |

TABLE 14

(Example 14 - TFMA removal from E-1234yf in the presence of fluoride)

| Base | KOH (85 wt %) 5.1 g + 0.06 g KF |
|---|---|
| Base concentration (mol/l) | 1.51 |
| Temperature (° C.) | 60 |

| Time (mins) | TFMA (wt %) | E-1234yf (%) |
|---|---|---|
| 0 | 0.50 | 98.96 |
| 60 | 0.17 | 99.63 |

TABLE 15

(Example 15 - TFMA removal from E-1234yf in the absence of fluoride)

| Base | KOH (85 wt %) 5.1 g |
|---|---|
| Base concentration (mol/l) | 1.51 |
| Temperature (° C.) | 60 |

| Time (mins) | TFMA (wt %) | E-1234yf (%) |
|---|---|---|
| 0 | 0.50 | 98.96 |
| 60 | 0.17 | 99.59 |

It can be seen that treatment with a base is very effective in reducing the absolute concentration of TFMA in its mixture with a range of HFOs, and increasing the HFO content of the mixture relative to TFMA overall.

The invention is defined by the claims.

The invention claimed is:

1. A process comprising contacting a composition comprising a (hydro)halocarbon and a compound of formula $R_f$—C≡CX with a basic solution comprising an hydroxide, alkoxide and/or an amide to reduce the concentration of $R_f$—C≡CX, wherein $R_f$ is a perfluorinated alkyl group and X is H, F, Cl, Br, or I, wherein the composition comprising a (hydro)halocarbon and a compound of formula $R_f$—C≡CX further comprises an undesired (hydro)halocarbon, and wherein contacting the composition with the basic solution reduces the concentration of the undesired (hydro)halocarbon by at least about 50% by weight.

2. The process according to claim 1, wherein the compound of formula $R_f$—C≡CX is 3,3,3-trifluoropropyne (trifluoromethylacetylene, TFMA).

3. The process according to claim 1, wherein the basic solution is an aqueous solution.

4. The process according to claim 1, wherein the basic solution comprises one or more of an alkali metal hydroxide, alkoxide or amide, an alkaline earth metal hydroxide or amide, or $NR_4OH$, wherein R is, independently, H, $C_{1-10}$ alkyl, aryl or arylalkyl group.

5. The process according to claim 1, wherein the basic solution contains one or more of potassium hydroxide (KOH), sodium hydroxide (NaOH) or calcium hydroxide ($Ca(OH)_2$).

6. The process according to claim 1, wherein the basic solution has a concentration of from about 0.1 to about 10 M.

7. The process according to claim 6, wherein the basic solution has a concentration of from about 0.2 to about 5 M.

8. The process according to claim 6, wherein the basic solution has a concentration of from about 0.5 to about 3 M.

9. The process according to claim 1, wherein the (hydro) halocarbon is a $C_{3-7}$ (hydro)haloalkene.

10. The process according to claim 9, wherein the $C_{3-7}$ (hydro)haloalkene is a hydrohalopropene.

11. The process according to claim 10, wherein the hydrohalopropene is a chlorotrifluoropropene and/or a tetrafluoropropene.

12. The process according to claim 11, wherein the chlorotrifluoropropene is $CF_3CH$=CHCl (HCFO-1233zd) and/or $CF_3CCl$=$CH_2$ (HCFO-1233xf).

13. The process according to claim 11, wherein the tetrafluoropropene is $CF_3CH$=CHF (HFO-1234ze) and/or $CF_3CF$=$CH_2$ (HFO-1234yf).

14. The process according to claim 1, wherein the process is carried out in the presence of a phase transfer catalyst.

15. The process according to claim 1, wherein the process is carried out at a temperature of from about 0 to about 100° C.

16. The process according to claim 15, wherein the process is carried out at a temperature of from about 10 to about 80° C.

17. The process according to claim 15, wherein the process is carried out at a temperature of from about 20 to about 60° C.

18. The process according to claim 1 having a contact time between the composition and the basic solution of from about 1 second to about 4 hours.

19. The process according to claim 18, wherein the contact time is from about 10 seconds to about 3 hours.

20. The process according to claim 18, wherein the contact time is from about 1 minute to about 180 minutes.

21. The process according to claim 1 wherein the composition is in the gas phase at least prior to contacting the basic solution.

22. The process according to claim 1 wherein the composition, prior to the contacting step, comprises at least about 90% by weight of the (hydro)halocarbon.

23. The process according to claim 22, wherein the composition, prior to the contacting step, comprises at least about 95% by weight of the (hydro)halocarbon.

24. The process according to claim 1 wherein the composition, prior to the contacting step, contains about 10000 ppm or less of the compound of formula $R_f$—C≡CX.

25. The process according to claim 24, wherein the composition, prior to the contacting step, contains about 5000 ppm or less of the compound of formula Rf-C≡CX.

26. The process according to claim 24, wherein the composition, prior to the contacting step, contains about 1000 ppm or less of the compound of formula Rf-C≡CX.

27. The process according to claim 1 wherein the amount of the compound of formula $R_f$—C≡CX in the composition is reduced by at least about 50% by weight.

28. The process according to claim 27, wherein the amount of the compound of formula Rf-C≡CX in the composition is reduced by at least about 70% by weight.

29. The process according to claim 27, wherein the amount of the compound of formula Rf-C≡CX in the composition is reduced by at least about 90% by weight.

30. The process according to claim 1 wherein following the contacting step, the resulting composition contains from 0 to about 500 ppm of the compound of formula $R_f$—C≡CX.

31. The process according to claim 30, wherein following the contacting step the resulting composition contains from 0 to about 100 ppm of the compound of formula Rf-C≡CX.

32. The process according to claim 30, wherein following the contacting step the resulting composition contains from 0 to about 10 ppm of the compound of formula Rf-C≡CX.

33. The process according to claim 1 wherein the undesired (hydro)halocarbon is selected from the group consisting of pentafluoropropenes, pentafluoropropanes, chlorotetrafluoropropanes, hexafluoropropanes and mixtures thereof.

34. The process according to claim 1 wherein the undesired (hydro)halocarbon is one or more of $CF_3CFH=CFH$ (HFO-1225ye), $CF_3CFHCFH_2$ (HFC-245eb), $CF_3CHF_2CF_2H$ (HFC-245fa), $CF_3CF_2CH_3$ (HFC-245cb), $CF_3CFClCH_3$ (HCFC-244bb) and $CF_3CFHCF_2H$ (HFC-236ea).

35. The process according to claim 1 wherein the amount of the undesired (hydro)halocarbon in the composition is reduced by at least about 50% by weight.

36. The process according to claim 35, wherein the amount of the undesired (hydro)halocarbon in the composition is reduced by at least about 90% by weight.

37. The process according to claim 1 wherein following the contacting step, the resulting composition contains from 0 to about 500 ppm of the compound of the undesired (hydro)halocarbon.

38. The process according to claim 37, wherein following the contacting step, the resulting composition contains from 0 to about 100 ppm of the compound of the undesired (hydro)halocarbon.

39. The process according to claim 37, wherein following the contacting step, the resulting composition contains from 0 to about 10 ppm of the compound of the undesired (hydro)halocarbon.

40. The process according to claim 1 wherein the composition is a product stream from a process for producing the (hydro)halocarbon.

41. The process according to claim 40 combined with one or more additional purification steps.

* * * * *